United States Patent [19]
Anderson

[11] 4,088,561
[45] May 9, 1978

[54] APPARATUS FOR ELECTROPHORESIS SEPARATION

[75] Inventor: Norman L. Anderson, Willowbrook, Ill.

[73] Assignee: The United States of America as represented by the United States Department of Energy, Washington, D.C.

[21] Appl. No.: 810,443

[22] Filed: Jun. 27, 1977

[51] Int. Cl.$^2$ .................... G01N 27/26; G01N 27/28
[52] U.S. Cl. ........................ 204/299 R; 204/180 G
[58] Field of Search .................. 204/180 G, 299; 23/230 B

[56] References Cited

U.S. PATENT DOCUMENTS

| | | | |
|---|---|---|---|
| 3,255,100 | 6/1966 | Raymond | 204/180 G |
| 3,719,580 | 3/1973 | Roberts et al. | 204/299 |
| 3,751,357 | 8/1973 | Rains | 204/299 |
| 3,847,788 | 11/1974 | Wallace | 204/301 |
| 3,888,758 | 6/1975 | Saeed | 204/299 |

*Primary Examiner*—Arthur C. Prescott
*Attorney, Agent, or Firm*—Dean E. Carlson; Frank H. Jackson; Hugh W. Glenn

[57] ABSTRACT

An apparatus is disclosed for simultaneously performing electrophoresis separations on a plurality of slab gels containing samples of protein, protein subunits or nucleic acids. A reservoir of buffer solution is divided into three compartments by two parallel partitions having vertical slots spaced along their length. A sheet of flexible, electrically insulative material is attached to each partition and is provided with vertical slits aligned with the slots. Slab-gel holders are received within the slots with the flexible material folded outwardly as flaps from the slits to overlay portions of the holder surfaces and thereby act as electrical and liquid seals. An elongated, spaghetti-like gel containing a sample of specimen that was previously separated by isoelectric focusing techniques is vertically positioned along a marginal edge portion of the slab gel. On application of an electrical potential between the two outer chambers of buffer solution, a second dimensional electrophoresis separation in accordance with molecular weight occurs as the specimen molecules migrate across the slab gel.

10 Claims, 6 Drawing Figures

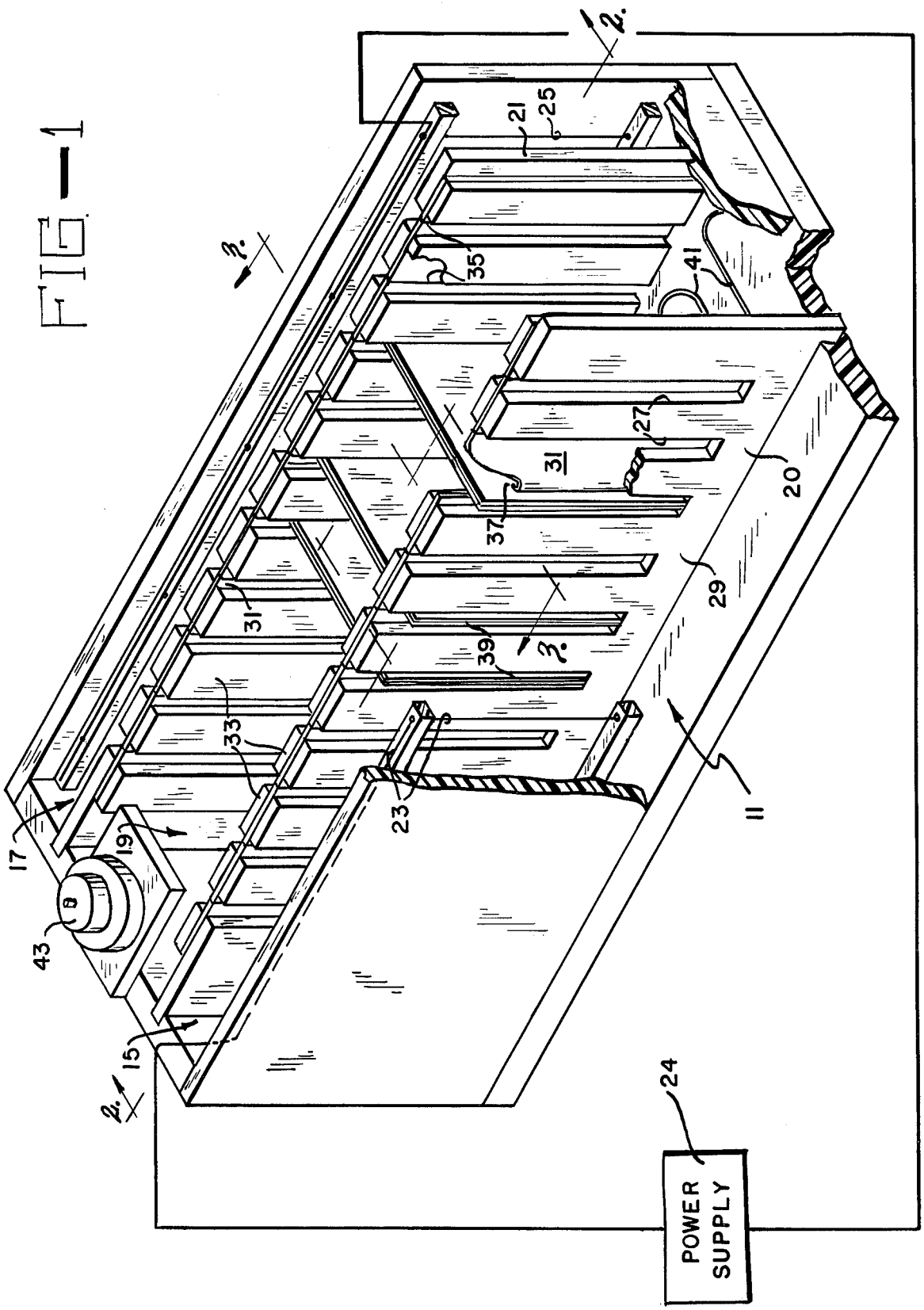

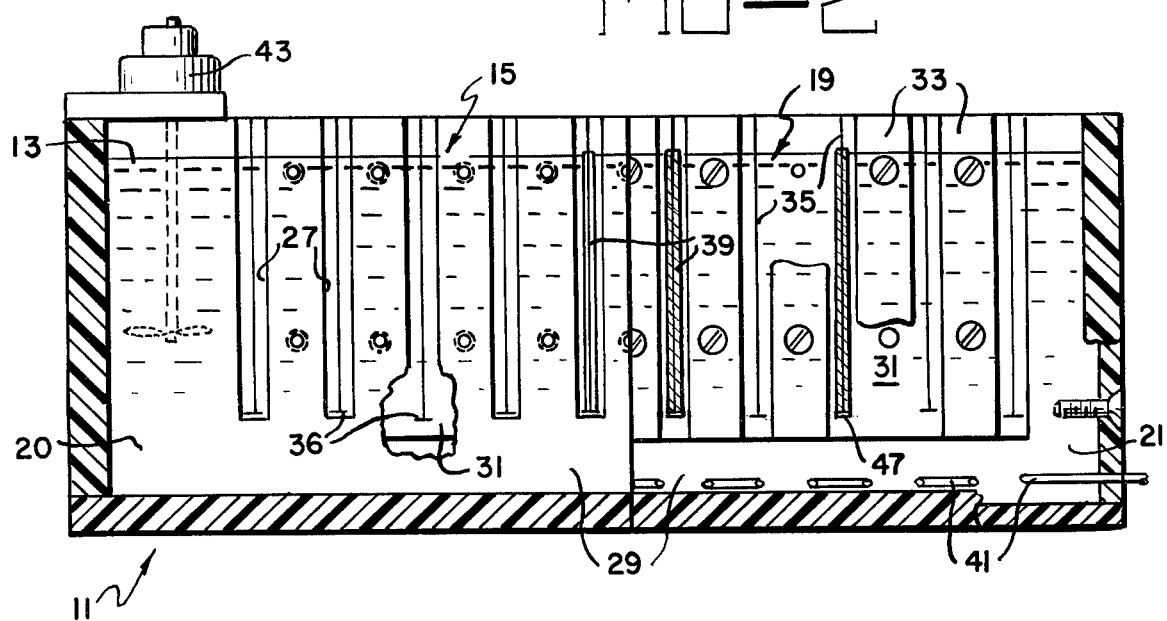
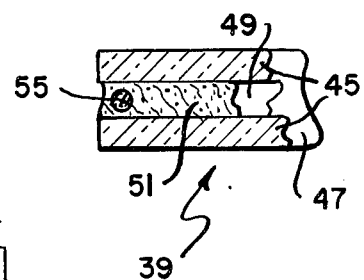
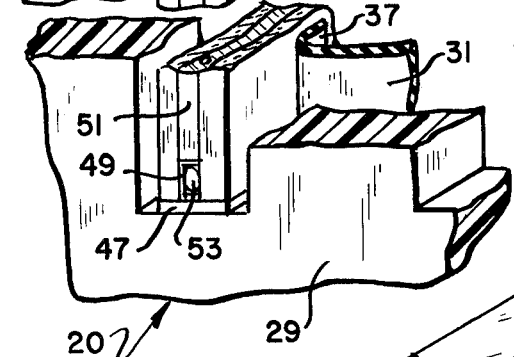
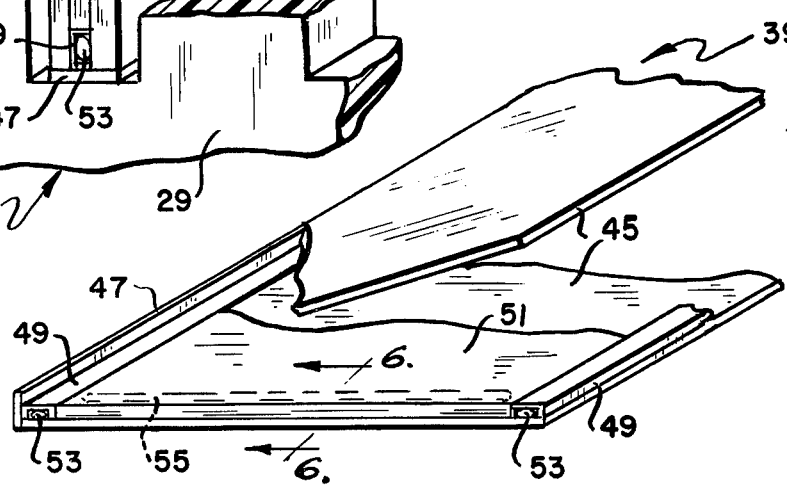

APPARATUS FOR ELECTROPHORESIS SEPARATION

CONTRACTUAL ORIGIN OF THE INVENTION

The invention described herein was made in the course of, or under, a contract with the U.S. ENERGY RESEARCH AND DEVELOPMENT ADMINISTRATION.

BACKGROUND OF THE INVENTION

The present invention relates to a device for the electrophoresis separation of material such as proteins, protein subunits and nucleic acids. The device is used as the second separation in a two-dimensional separation system which begins with the isoelectric separation of species along a thin, elongated or spaghetti-like gel medium. In the original separation proteins ammino acids or other specimen material migrate, usually downwardly, to a previously established pH point within the gel at which the species of sample is electrically neutral, that is to its isoelectric point. Separation of these types are quite well known and when combined with a second dimension electrophoresis separation, the highest resolution of protein and protein subunits thus far developed can be achieved. In the second electrophoresis separation sample species migrate through a gel acting as a sieve to a point determined by their molecular weight.

The initial isoelectric separation is performed in a known manner. An isoelectric focusing gel of, for instance, acrylamide with catalyst, focusing compounds and crosslinking agents is formed and subjected to a prefocusing electrical potential between an alkali and an acid buffer solution, e.g., NaOH and $H_3PO_4$. This establishes a pH gradient along the spaghetti-like isoelectric gel. The sample material is applied into the top of the gel containment tube and permitted to migrate under the influence of an electrical potential between the upper and lower buffer solutions. After a period of about 20 hours, the various sample species will have migrated to isoelectric points of neutral charge. The samples can then be removed from their containment tubes in preparation for a second dimensional electrophoresis separation.

The separation in the second dimension is performed by a sodium dodecyl sulfate electrophoresis within a two-dimensional acrylamide gel. Gel compositions are well known and include polymerization as well as cross-linking agents along with a gel buffer. Gels of this type have previously been assembled manually between glass plates with laboratory clamping devices and subjected to electric current between separate upper and lower buffer soluations. Such an apparatus and procedure is sufficient for performing occasional electrophoresis separations of protein specimens but is quite cumbersome and time consuming when a large number of samples must be run, as in genetic screening surveys and clinical diagnosis applications. The prior art devices for electrophoresis separations have been limited to one or at most two slab-gel media for sample resolution. These devices quite often leak buffer solution at gasketed seals where the slab-gel holders passed from the upper buffer solution container. Because of these limitations only a few slab gels could be subjected to electrophoresis at one time and substantial amounts of attention have been required by laboratory attendants.

PRIOR ART STATEMENT

The following publications describe an apparatus for slab-gel electrophoresis and a two-dimensional electrophoresis technique for proteins.

Reid and Bieleski, "A Simple Apparatus for Vertical Flat-Sheet Polyacrylamide Gel Electrophoresis," *Analytical Biochemistry*, 22, 374–381 (1968).

This article describes an apparatus for separating complex mixtures with proteins and nucleic acids within a slab-gel medium. The electrophoresis is carried out between an upper and a lower buffer trough. The slab-gel holder is clamped onto the face of a vertical table with a gasket in place to prevent leakage of buffer solution into the lower buffer trough. Since the slab-gel assembly must be clamped against a vertical member and a gasket, only one slab-gel sample is conveniently handled at a time in such an apparatus.

Studier, "Analysis of Bacteriophage T7 Early RNAs and Proteins on Slab Gels," *Journal of Molecular Biology*, 79, 237–248 (1973).

This publication describes a technique for slab-gel electrophoresis separation for the separation and identification of RNAs and proteins of the bacteriophage T7 in a polyacrylamide gel. As indicated on page 240, the electrophoresis apparatus disclosed in this publication is quite similar to that shown by Reid and Bieleski. It is necessary to provide a liquid seal on the slab-gel holder within the upper buffer chamber. This is accomplished by dripping melted agar into notches provided on the surface of the glass plate holder and the buffer chamber. The agar solidifies to form a seal.

O'Farrell, "High Resolution, Two-Dimensional Electrophoresis of Protein," *The Journal of Biological Chemistry*, Vol. 250, No. 10, 4007–4021, May 25, 1975.

This article describes a method of performing a two-dimensional electrophoresis separation in polyacrylamide gel to obtain an extremely high resolution of protein. An apparatus as presented in Reid and Bieleski and modified by Studier is used.

None of these articles describe or show the apparatus which applicants have claimed in the present application. In particular, they do not teach the structure of the electrophoresis apparatus summarized below.

SUMMARY OF THE INVENTION

In view of the difficulties associated with prior art devices, it is an object of the present invention to provide an apparatus for electrophoresis separations that can conveniently accommodate a plurality of slab gels in a single electrophoresis operation.

It is a further object to provide such an electrophoresis apparatus which minimizes or eliminates difficult problems of buffer solution leakage.

It is another object to provide such an electrophoresis apparatus in which a large number of slab-gel holders can readily be assembled with samples for processing.

It is also an object to provide an electrophoresis apparatus with slab-gel holders which permit improved consistency in slab-gel thickness.

In accordance with the present invention an apparatus for electrophoresis separation of samples within a slab gel is provided. The apparatus includes a reservoir for containing a buffer solution divided into an inner and two outer compartments with first and second lengthwise partitions. Each of the partitions include aligned vertical slots from their top surfaces throughout a portion of their height leaving a continuous bottom margin. A plurality of slab-gel holders are disposed in aligned pairs of slots within the partitions. The slab-gel holders have vertical edge portions with exposed gel edges at their sides facing into the outer two reservoir compartments for electrically contacting the buffer solution. The sample for electrophoresis is disposed in one of these vertical edge portions. The outer, major surfaces of the slab-gel holders slidably contact flaps or other type surfaces of electrically insulative material within the vertical slots to provide a high resistance to electrical current flow through the buffer solutions. Each of the outer buffer compartments are provided with electrodes for establishing a difference of electrical potential between the buffer solutions in the two outer compartments. This directs an electrical current through the slab-gel medium for electrophoresis of sample protein, subprotein groups, amino acids, nucleic acids, or other sample material across the slab gel.

In more specific aspects of the invention the same buffer solution is filled into the three buffer compartments to the same level below the upper surface of the slab-gel holder. Also, this slab-gel holder can include two plates with a mutually connected hinge at a horizontal edge. Spacer strips are attached to inner surfaces of one of the plates with a fillet of adhesive material disposed within an underneath side groove. Such strips attached in this manner provide improved consistency to the slab-gel thicknesses.

BRIEF DESCRIPTION OF THE DRAWINGS

The present invention is illustrated in the accompanying drawings wherein:

FIG. 1 is a perspective view of an apparatus for electrophoresis separation within a plurality of slab gels.

FIG. 2 is a cross sectional side view of the apparatus of FIG. 1.

FIG. 4 is a perspective view of a slab gel holder with the sample and gel in place.

FIG. 5 is an enlarged, fragmentary view in perspective showing the sample holders in place within the apparatus.

FIG. 6 is a fragmentary, sectional view showing the sample within the sample holder.

DETAILED DESCRIPTION OF THE PREFERRED EMBODIMENT

Figure 3:
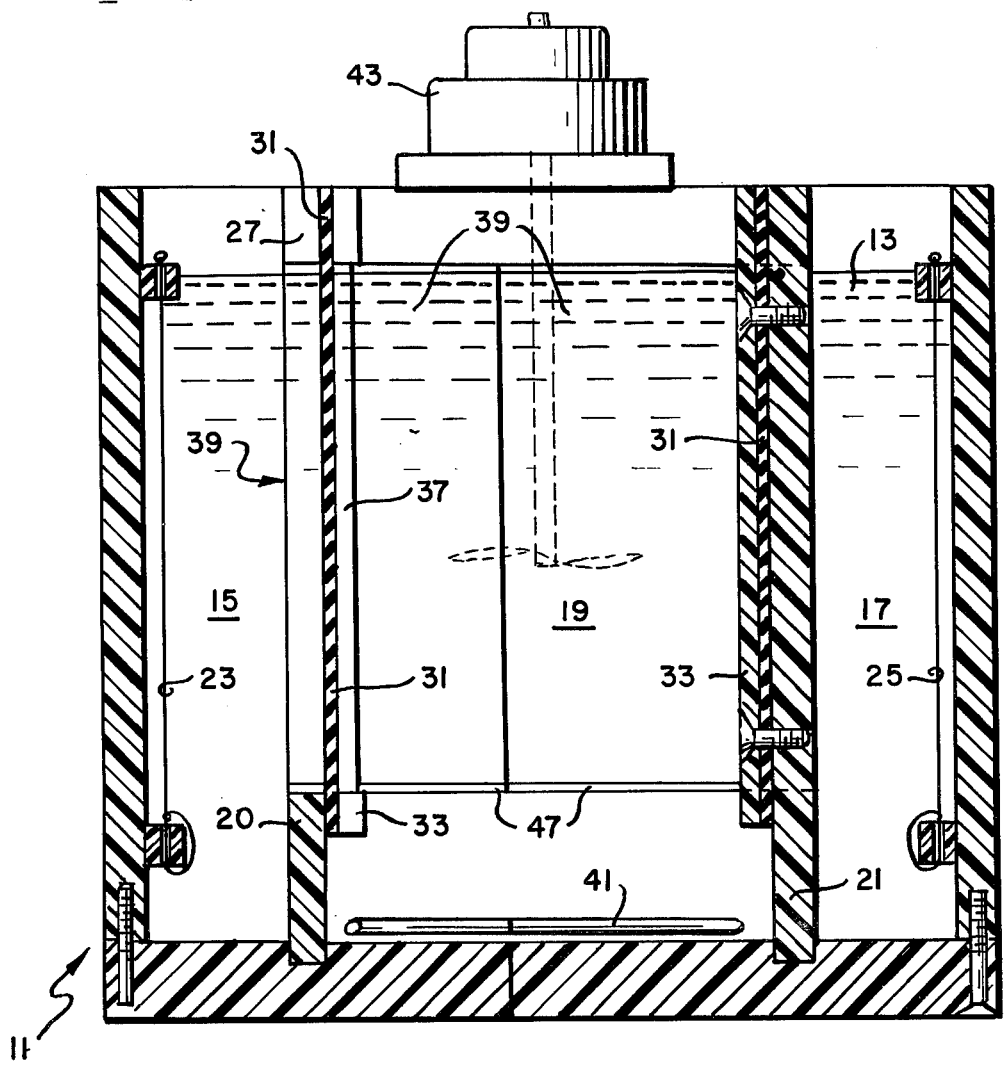
FIG. 3 is a sectional, end view of the FIG. 1 apparatus.

Referring to FIGS. 1, 2, and 3, a reservoir 11 containing a buffer solution 13 is illustrated. For clarity, buffer solution 13 is not shown in FIG. 1. The reservoir 11 is divided lengthwise into two outer compartments 15 and 17 on either side of an inner compartment 19 by two parallel partitions 20 and 21. The partitions are sealingly mounted into the end and bottom walls of the reservoir.

Electrodes 23 and 25 made up of wire links and supports or other suitable structure are placed in contact with the buffer solution within compartments 15 and 17 respectively. Reservoir 11 and partitions 20 and 21 are constructed of an electrically insulative material such as lucite so that an electrical potential from power supply 24 applied at electrodes 23 and 25 will establish a difference of potential between the buffer solution within compartments 15 and 17. Lucite, glass and other like materials are well suited as construction materials as they are both electrically insulative and transparent to permit visual observations during operation.

Partitions 20 and 21 are provided with a plurality of slots 27 which extend dowwardly from the top surface of the partitions to a location short of the partition bottom, leaving a solid portion 29 lengthwise along the bottom of the partition. A sheet of flexible, electrically insulative material, e.g., rubber, silicon rubber or Tygon, 31 is held over the inwardly facing surfaces of the partitions which define inner chamber 19 by suitable plastic strips 33. Sheets 31 extend over a sufficient portion of the partition height to cover the full height of slots 27. The unsupported portions of sheets 31 that directly pass over slots 27 are provided with centrally located slits 35 to permit these portions of the sheets to open up into flaps 37 (see FIG. 5) within slots 27 or between strips 33. The lower end of slits 35 can be provided with an inverted T slit portion 36 (FIG. 2) to facilitate the opening of flaps 37.

A plurality of sample holders 39 are positioned within corresponding, facing slots 27 of partitions 20 and 21. Flaps 37 can be directed towards the same side by inserting the sample holders and moving them in a lateral direction. When all of the sample holders are in place to the bottom of slots 27 with the electrically insulative flaps 37 tightly pressed to major surfaces of the sample holders, a substantial electrical resistance is imposed to electrical current flow through the buffer solution from chamber 15 to chamber 17. All three chambers 15, 17 and 19 are filled with buffer solution 13 but only to a level slightly below the top surfaces of sample holders 39 as shown in FIG. 3.

A cooling coil 41 is provided within the inner buffer chamber 19 along with suitable agitation means 43 such as a motor driven propeller blade or a circulation pump. The heat resulting from current flow through the samples and through the buffer solution at sealing and electrically insulating flaps 37 can be removed from the buffer solution within the inner chamber 19.

The sample holders 39, shown in more detail in FIGS. 4, 5, and 6 comprise two rigid plate members 45 of glass or other suitable transparent and electrically insulative material. Plates 45 are hinged together at one edge surface by a flexible strip 47 that extends widthwise across the plates. Strip 47 is of a suitable tough and electrically insulative material such as rubber, silicon rubber or other rubber-like material. It can be attached by strong silicon rubber glue to the glass plate edges. As more clearly shown in FIGS. 3 and 5, flexible strip 47 provides a liquid and electrically insulative seal at the bottom surface of slot 27 when the sample holder 39 is in place.

One or more spacer strips 49 are fixed on an inside surface of one of the sample holder plates 45. Strips 49 extend widthwise across the plate and provide a volume of consistent thickness for the slab gel 51. Strips 49 are of a rigid hard material such as polyvinyl chloride and can be adhesively attached to the plate surface by means of a fillet 53 of adhesive material disposed in an underneath side groove of strips 49. A commercially available room-temperature-vulcanizing, silicon rubber glue is sufficient for this purpose. Through use of the fillet of glue as means for attaching the strips to the sample plates, an improvement in thickness consistency is obtained for the various slab gels.

An elongated specimen or sample 55 is shown in FIGS. 4 and 6 extending across one edge surface of the slab gel between the spacer members 49. When installed in the apparatus, the sample is vertically positioned. The sample can include proteins, protein subunits, amino acids or nucleic acids that are to be separated by electrophoresis. The sample specimens can be contained within an elongated cylindrical or spaghetti-like gel and can be sealed with such as agarose gel into the edge surface of the slab gel. Alternatively, the samples can be pipeted onto a top edge of the slab gel and sealed with a suitable gel or gel-like material before rotating the sample holder to position the samples in a vertical orientation.

High resolution of proteins and other sample materials can be obtained through use of two-dimensional separations. In the first, the proteins are separated according to their isoelectric point by isoelectric focusing along a thin cylindrical gel within a small-diameter tube. The spaghetti-like gel containing the various proteins separated in accordance with their isoelectric point can be extruded from the tube and positioned along the edge surface of slab gel 51 as indicated at 55 in FIGS. 4 and 6. The proteins can then be separated along a second dimension across the slab width to provide additional resolution according to their molecular weight.

The procedures for carrying out such two-dimensional isoelectric and electrophoresis separations are well known and documented in the literature, for instance, see O'Farrell cited above. The gels for isoelectric focusing are prepared in small-diameter glass tubes, e.g. I.D. 1–3 mm, whose bottoms are initially sealed with paraffin. Merely by way of example, a focusing gel for the analysis of human serum proteins can include 8.25 g urea; 750 ul ampholyte (LKB), pH 3.5–10; 2 ml 30% by weight acrylimide in water plus 1.8% by weight bisacrylamide in water; 6 ml water; 300 ul Nonidet P-40 (NP-40-a detergent available from Particle Data Laboratories Ltd., Elmhurst, Ill.; 30 ul ammonium persulfate; and 20 ul N,N,N,N'-tetramethylethylenediamine (TEMED). This formula would yield a volume of about 15 ml which would be adequate for a battery of about 25 isoelectric focusing gels. This solution is degassed before adding the catalyst, TEMED, and loaded into the gel tubes for polymerization. The gel solution can be loaded with hypodermic needles or, more conveniently, by displacing the gel solution from a reservoir or well around the tube bottoms into the tubes. This latter technique can be accomplished merely by lowering a battery of gel tubes with their lower ends submerged in a well of unpolymerized gel into a reservoir of water or other liquid less dense than the gel solution. Polymerization is then allowed to proceed for about an hour.

Before adding the samples, the gels can be prefocused to establish a pH gradient along their length while applying a potential difference of about 200 V across the gel end portions. The gel ends can be submerged in dilute concentrations of about 0.02 M NaOH and 0.01 M $H_3PO_4$ at opposite ends. The samples of proteins or other material in, for instance, concentrated urea are introduced at the alkaline end of the isoelectric focusing tube which is then run at about 400 to 800 V for 1 to 20 hours as required to separate the individual proteins to their isoelectric points.

The isoelectric focusing gel is extruded, for instance with a hypodermic of water, into a sodium dodecyl sulfate solution (SDS) until equilibrium to soak out ampholytes. The spaghetti-like sample gels are then ready to be loaded into the slab gel sample holders 39 as indicated at 55 in applicant's FIG. 4.

The formulations of the slab gels illustrated at 51 in FIG. 4 are well known and are described in O'Farrell cited above. An acrylamide gel in uniform or in gradient concentration across the slab width can be employed. The best separation of proteins is achieved using an exponential acrylamide gradient gel.

The slab gel solutions in monomer form are filled into the sample holders 39 from a standard and commercially available gradient mixer, for instance a Reeve-Angel Gradient Former. The gradient mixture can provide a continuously varying concentration of, for instance acrylamide, during the filling operation. In order to prevent mixing of the gradient during filling, the holder can be supported with a corner adapted for introduction of the gel solution pointed downwardly. Filling can proceed at a gentle flow rate with the less dense material introduced first and the more highly concentrated acrylamide solution last. As the filling proceeds towards completion, the slab gel holder can be slowly rotated such that a consistent density gradient of acrylamide is formed across the slab gel. Filling may also proceed in like manner by introducing the acrylamide solution across the bottom edge surface from a flat V-shaped funnel to minimize mixing.

A typical slab gel solution prior to polymerization will include from about 5 to 22.5% by weight acrylamide, 0.1% by weight sodium dodecyl sulfate, 0.375 M tris (hydroxymethyl) aminomethane-HCl, pH 8.8 and the remainder water. Also included in small volume proportions are ammonium persulfate in water and the polymerization catalyst TEMED. A glycerol solution can be used instead of water where high concentrations of acrylamide are prepared. After allowing the gel to polymerize for about an hour, the residual unpolymerized gel mixture and water are removed from the gel surface. In some applications, a secondary butanol-water mixture can be added to the top of the gel before polymerization to insure a flat surface. The slab gel can then be completed by applying a stacking gel having a lower acrylamide concentration, e.g., 5% by weight or less, at the surface intended for the sample application. The use of the stacking gel is a well-known procedure for sharpening to a refractile thickness the individual volumes of proteins or other sample material previously separated in accordance with their isoelectric points.

The elongated sample gel formed as previously described can be stretched out on a suitable surface and rolled onto the top of the stacking gel between the two glass plates 45 of the sample holder 39. After smoothing into place, an overlay of an agarose is used to hold the sample gel in position. The equilibrium buffer previously used to soak out the ampholytes in the isoelectric focusing gel can contain bromphenol blue or another suitable dye to make the sample easily visible. Thus the progress of the sample across the slab gel during electrophoresis can be easily followed.

The slab gel holders 39 with the slab gels 51 and samples 55 in place are slid into position into slots 27 within the partitions 20 and 21. The electrically insulative flaps 37 are aligned against the major surfaces of the sample holders. If some of the pairs of slots 27 are not filled, the flexible, electrically insulative sheets 31 close at slits 35 to minimize electrical contact and fluid flow between the buffer solutions within the three compartments 15, 17 and 19. In most applications, the isoelectrically focused samples will be aligned along a vertical gel edge in contact with the buffer solution of the same outer compartment. The flaps 37 open sufficiently to accept the sample holders as they are inserted and seal against the holder surfaces to prevent electrical leakage.

The reservoir 11 is filled preferably with a single buffer solution in all three of its compartments 15, 17 and 19 to a level below the top surface of holder 39. When serum proteins are being run, this solution can typically be about 0.02 to 0.2 M tris(hydroxymethyl), aminomethaneglycine (pH 8.3) in water with about 0.05% by weight SDS. Other known buffer solutions might also be used in one or more of the compartments. However, where different buffer solutions are used in different compartments, some interdiffusion may occur between flaps 37 and holders 39.

The power supply 24 provides about 200 to 500 V direct current at up to about one amp for 10 sample gels run in parallel. The electrophoresis separation can continue for about 4 to 8 hours to result in a second dimensional separation of the sample proteins, protein subunits or nucleic acids in accordance with their molecular weight. The sieving action of the increasing gradient density of acrylamide accomplishes this separation.

In this second dimensional separation, the dodecyl sulfate (SDS) attaches to the proteins and protein subgroups to negate the charge or isoelectric effect which would otherwise affect migration. Consequently, each molecular species migrates to a location determined by its size or molecular weight. In a transparent tank of glass or lucite the movement of the dye front can be readily observed for a plurality of gels and the run can be terminated when the dye reaches the opposite end of the slab-gel width.

The resulting slab gel will include a sample material that is resolved in accordance with its isoelectric characteristics in one dimension and in accordance with its molecular weight in a second dimension. The individual sample species can be located by suitable and well-known staining and destaining techniques such as with coomassie blue in 12% trichloroacetic acid followed by destaining in several changes of 7% acetic acid. In other applications, radioisotopes can be included in the various sample species and autoradiographs made by disposing the slab gels near suitable film.

The slab gels, having their protein species separated in two dimensions and their locations identified by the techniques shown above, can then be compared with slag gels containing previously resolved control samples. In other instances, the slab gels may be compared with other unknown specimens subjected to the two-dimensional resolution to provide qualitative results. Photographic and autoradiographic images of the resolved samples in two dimensions can be analyzed by computerized techniques to assist in handling large numbers of samples.

Applicant's apparatus for permitting the simultaneous second dimensional resolution of a plurality of slab gels without buffer solution leakage problems presents new opportunities for two-dimensional protein resolution. For instance, genetic screening applications in which serum samples are collected from a large number of individuals for the detection of mutants and other genetic changes can be conveniently carried out with applicant's apparatus. Often mutant proteins are detected by changes in their charge to their OH and H groups. The electrophoresis apparatus described herein would be used to identify by molecular weight a protein which had found its isoelectric point at a new location due to its mutated charge. Studies of this nature are extremely important in determining the effect of environmental pollutants, both chemical and radioactive.

The apparatus of the present invention may also have clinical applications, for instance, in the identification of loss of transferrin which carry out iron transfer within blood samples. Wilson's disease, through identification of low or lack of ceruloplasmin, might also be identified. Through use of various densitometers that are known for quantitating the amount of stain, and hence the amounts of protein, other diagnostic procedures relating to heart attacks and arteriosclerosis might be developed. For example, blood samples could be run to compare the amounts and types of serum lipoproteins between normal blood samples and those of patients possibly having these type problems. Through use of applicant's apparatus, new techniques may arise for redescription and redefinition of human disease in terms of the pieces of which cells are made.

It will be clear that the various solutions and gels that are employed are well known and can be substituted with other materials such as those that are disclosed and described in the above-cited publications. In addition, various other procedures for operating the novel apparatus of the present invention might be suggested by those skilled in the art. It will also be clear that various materials of construction and known construction techniques will occur to the technician to adapt applicant's novel apparatus to other applications within the scope of the invention as set forth in the claims.

The embodiments of the invention in which an exclusive property or privilege is claimed are defined as follows:

1. An apparatus for slab-gel electrophoresis comprising:
   a reservoir for containing a buffer solution;
   first and second partitions, each having corresponding vertical slots from their top surfaces throughout a portion of their height, sealingly disposed in parallel along the length of the reservoir to form two outer and an inner parallel compartments, the vertical slots of each partition being in alignment with the slots of the other partition to form an array of opposing pairs of corresponding slots;
   a plurality of slab-gel holders, each disposed in a pair of slots within the partitions, the holders having vertical edge portions with exposed slab-gel edges facing into the outer two reservoir compartments for contacting buffer solution;
   a sample for electrophoresis placed at one of the exposed slab-gel edges;
   electrically insulative sealing means interposed between the vertical slots of the two partitions and the sample holders; and
   electrode means within the two outer compartments for establishing a difference of electrical potential between the buffer solutions within the two outer compartments to pass an electrical current for an electrophoresis separation of the sample from one vertical edge surface of a slab-gel to the opposite vertical edge surface.

2. The apparatus of claim 1 wherein the same buffer solution is filled in the inner and two outer compartments to essentially the same level below the top surface of the slab-gel holders.

3. The apparatus of claim 1 wherein the reservoir, partitions and slag-gel holders are of electrically insulative material.

4. The apparatus of claim 1 wherein at least one of the slag-gel holders comprises a pair of rigid plates of electrically insulative material having a mutual hinge connection at one edge to permit pivotal positioning of inwardly facing major surfaces for receiving a slab gel, and having on one of the plates, at an inwardly facing major surface, spacer means for providing a consistent thickness for the contained slab gel.

5. The apparatus of claim 4 wherein the spacer means are horizontal strips of uniform thickness attached to an inwardly facing surface of one of the pair of holder plates, each of the strips having a groove containing a fillet of adhesive material at its underneath surface disposed against the plate surface to minimize thickness deviations resulting from inconsistencies in the adhesive material.

6. The apparatus of claim 4 wherein said slab-gel holders are disposed in the apparatus with the hinge connection at a lower horizontal edge of the holder against the bottom of the vertical slots within the first and second partitions, the hinge connection comprises a strip of flexible rubber-like material to provide an electrical and liquid seal between the buffer solution in the outer and the inner compartments.

7. The apparatus of claim 1 wherein at least one of the slab-gel holders contains, at its exposed surface, a vertically disposed, elongated gel containing sample substances that are separated along the length of the elongated gel in accordance with their isoelectric characteristics.

8. The apparatus of claim 1 wherein the partitions each comprise a slotted plate with a sheet of flexible electrically insulative material attached to a major surface to electrically seal between the inner and outer compartments, the sheet having vertical slits in portions exposed within the slots for receiving the slab-gel holders.

9. The apparatus of claim 8 wherein the slab-gel holders are positioned within the vertical slits such that flap portions of the electrically insulative sheet overlay surface portions of the holders and thereby provide electrically insulative means between the buffer solutions within the two outer compartments and the inner compartments.

10. The apparatus of claim 1 wherein means for cooling and agitating the liquid within the inner compartment are provided.

* * * * *